(12) United States Patent
Mastrodonato

(10) Patent No.: US 8,431,601 B2
(45) Date of Patent: *Apr. 30, 2013

(54) TOPICAL COMPOSITIONS COMPRISING TELMESTEINE FOR TREATING DERMATOLOGICAL DISORDERS

(75) Inventor: Marco Mastrodonato, Milan (IT)

(73) Assignee: Sinclair Pharmaceuticals Ltd., Surrey (GB)

(*) Notice: Subject to any disclaimer, the term of this patent is extended or adjusted under 35 U.S.C. 154(b) by 539 days.

This patent is subject to a terminal disclaimer.

(21) Appl. No.: 12/575,848

(22) Filed: Oct. 8, 2009

(65) Prior Publication Data

US 2010/0130568 A1    May 27, 2010

Related U.S. Application Data

(63) Continuation of application No. 10/575,023, filed as application No. PCT/EP2004/011228 on Oct. 7, 2004, now abandoned.

(30) Foreign Application Priority Data

Oct. 9, 2003 (IT) .............................. MI2003A1941

(51) Int. Cl.
*A61K 31/426* (2006.01)
*C07D 277/06* (2006.01)

(52) U.S. Cl.
USPC .......................................... 514/365; 548/201

(58) Field of Classification Search .................. None
See application file for complete search history.

(56) References Cited

U.S. PATENT DOCUMENTS

| 4,874,776 | A | 10/1989 | Quadro |
| 7,262,180 | B2 | 8/2007 | Mastrodonato et al. |
| 2006/0247183 | A1 | 11/2006 | Mastrodonato et al. |
| 2008/0015155 | A1 | 1/2008 | Mastrodonato et al. |
| 2008/0114057 | A1 | 5/2008 | Mastrodonato et al. |

FOREIGN PATENT DOCUMENTS

WO    WO-03/084553    10/2003

OTHER PUBLICATIONS

Serra et al., "In vitro evaluation of olive- and grape-based natural extracts as potential preservatives for food" Innovative Food Science and Emerging Technologies (2008) vol. 9 pp. 311-319.*

Ashcroft et al., "Therapeutic strategies for psoriasis", Journal of Clinical Pharmacy and Therapeutics, 25:1-10 (2000).
Gianotti, A., "Telmestein and variations in blood concentrations of lipoprotein A" La Clinical terepeutica, vol. 145(10):283-285 (1994).
Greaves et al., "Treatment of Psoriasis", N. Engl. J. Med., 332:581-588 (1995).
International Search Report for PCT/EP2004/011228 dated Mar. 24, 2005.
International Preliminary Report on Patentability for PCT/EP2004/011228 dated Jan. 1, 2006.
Langer, "New Methods of Drug Delivery", Science, 249:1527-1533 (1990).
The Merck Manual of Diagnosis and Therapy, published 1999 by Merck Research Laboratories, Section 10, Dermatologic Disorders, pp. 777-786.
Merriam-Webster's Collegiate Dictionary, Tenth Edition, published 1999 by Merriam-Webster, Incorporated, p. 924.
Nevitt et al., "Psoriasis in the community: prevalence, severity and patients' beliefs and attitudes towards the disease", British Journal of Dermatology, 135:533-537 (1996).
Piccioni et al., "Experimental study on some properties of N-carbethoxy-4-thiazolidine" Revista Italiana Di Biologia E Medicina, 11:123-127 (1991).
Remington: The Science and Practice of Pharmacy 20$^{th}$ Edition (2000) Published by the Philadelphia College of Pharmacy and Science, Edited by Alfonso R. Gennaro et al., pp. 836-844 and 917-918.
Roenigk et al., "Methotrexate in psoriasis: Revised guidelines", J. Am. Acad. Dermatol., 19:145-156 (1988).
Stern, "Epidemiology of Psoriasis", Dermatologic Clinics, 13:717-722 (1995).
Stern et al., "The Carcinogenic Risk of Treatments for Severe Psoriasis", Cancer, 73:2759-2764 (1994).
Zhai et al., "Efficacy of a Topical Agent, MAS063D ('Atopiclair'), in the Treatment of Sodium Lauryl Sulphate-Induced Irritant Contact Dermatitis", Exogenous Dermatology, 2:301-305 (2003).

* cited by examiner

*Primary Examiner* — Eric S Olson
(74) *Attorney, Agent, or Firm* — Marshall, Gerstein & Borun LLP

(57) ABSTRACT

This invention relates to topical compositions, such as creams and lotions, that comprise or consist essentially of Telmesteine, or a pharmaceutically acceptable salt thereof, as the active ingredient, and methods for their use in treating a variety of dermatological diseases and disorders, including atopic, dermatitis (eczema), allergic contact dermatitis. seborrheic dermatitis, radiation dermatitis, psoriasis, xerosis and atopy.

10 Claims, No Drawings

TOPICAL COMPOSITIONS COMPRISING TELMESTEINE FOR TREATING DERMATOLOGICAL DISORDERS

This application is a continuation of U.S. patent application Ser. No. 10/575,023, filed Jan. 22, 2007, now abandoned which is a U.S. national phase application pursuant to 35 U.S.C. §371 of International Application No. PCT/EP2004/011228, filed Oct. 7, 2004, which claims benefit of priority of Italian Patent Application No. MI2003 A001941, which was filed Oct. 9, 2003. The entire disclosure of each of the foregoing applications is incorporated herein by reference.

FIELD OF THE INVENTION

This invention relates to topical compositions, such as creams and lotions, that comprise or consist essentially of Telmesteine as the active ingredient and methods for their use in treating, preventing, or ameliorating a variety of dermatological diseases and disorders, including atopic dermatitis (eczema), allergic contact dermatitis, seborrheic dermatitis, radiation dermatitis, psoriasis, xerosis and atopy.

BACKGROUND OF THE INVENTION

Telmesteine or N-carbethoxy-4-thiazolidin-carboxylic acid, disclosed in Italian Patent No. 1,215,469, has the following structure:

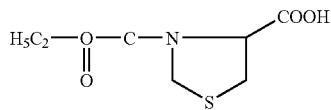

The presence of the carbethoxy group makes the molecule very lipophilic as compared to a similar molecule lacking the carbethoxy group. Methods for making Telmesteine are described, for example, in U.S. Pat. No. 4,874,776, the disclosure of which is incorporated by reference herein in its entirety.

Telmesteine, and alkali and alkali-earth of basic amino acid salts thereof, have mucolytic activity and inhibit elastase and collagenase, and are known to be useful in the treatment of respiratory tract disorders such as emphysema and fibrosis.

Dermatitis is a superficial inflammation of the skin, characterized by vesicle formation, erythema, edema, oozing, scaling or crusting lesions, and intense itching. Different types of dermatitis can be distinguished: contact dermatitis, caused by irritants in contact with the skin or by non-irritating substances, to which the subject is allergic; atopic dermatitis, characterized by strong itching and chronic course; seborrheic dermatitis, a scaling disease mainly affecting the face and scalp. In principle, the treatment consists in removing the etiological agent; however, frequently such agent cannot be identified or removed.

One particular form of dermatitis is psoriasis, which is a chronic, inflammatory, hyperproliferative skin disease that affects approximately 1-2% of the general population with men and women affected in equal numbers (Nevitt, G. J. et al., 1996, British J. of Dermatology 135:533-537). Approximately 150,000 new cases of psoriasis and approximately 400 deaths from psoriasis are reported each year (Stern, R. S., 1995, Dermatol. Clin. 13:717-722). The impact of psoriasis on the lives of patients goes beyond the effects on their physical appearance; it can also negatively impact their physical capacity and longevity. The most common type of psoriasis is chronic plaque syndrome. The condition is chronic for many sufferers and consists of periods of remission and relapse during the course of the disease (Ashcroft, D. M., et al., 2000, J. of Clin. Pharm. And Therap. 25:1-10). Psoriasis is characterized by indurated, erythematous scaling plaques most commonly located on the scalp or the extensor aspects of the elbows and knees, but may occur at any skin site.

Traditionally, treatment of such dermatitis has been based on corticosteroids, which involves well known side effects such as reduced immune defense resulting in a secondary bacterial infection, particularly of fungi or *Candida*. Further, such treatment requires frequent suspension of the treatment, and such treatment cannot be used during the exudative acute phase of the dermatitis. Furthermore, prolonged use of corticosteroids should be avoided, especially in pregnant women and in children, as systemic side effects can occur.

The present treatment options currently available for psoriasis include topical agents, phototherapy and systemic agents. Topical treatments are first-line therapy for patients with mild to moderate plaque psoriasis. Systemic treatment is generally prescribed for severe cases of psoriasis where topical therapy is either impractical or ineffective. Phototherapy can be administered either alone or in combination with either topical or systemic agents. In selecting a suitable treatment, consideration should be given to the overall severity of the disease, the body areas involved, that patient's age, sex, general health, previous treatment and preferences.

Topical agents available for the treatment of psoriasis include emollients, keratolytics, coal tar, topical corticosteroids, dithranol (anthralin), topical vitamin D3 analogues and tazarotene. Unfortunately, these topical agents are associated with side effects such as irritation, toxicity and possible carcinogenicity (Ashcroft, D. M., et al., 2000, J. of Clin. Pharm. and Therap. 25:1-10).

Examples of phototherapy for psoriasis include ultraviolet B radiation (UVB) phototherapy and ultraviolet A photochemotherapy (PUVA). UVB phototherapy employs broadband (290-320 nm) sources and is useful in the management of moderate to severe psoriasis and is generally administered to patients whose disease is refractory to topical therapy. Treatment is usually administered two to three times a week with coal tar often being applied prior to exposure. UVB phototherapy must be carefully regulated, however, due to the short-term risks of erythema and vesiculation and the long-term risks or premature skin aging. PUVA therapy combines long wave (320-400 nm) ultraviolet A irradiation with oral or topical administration of psoralens The two psoralens traditionally used, 5- and 8-methoxypsoralen (MOP) are believed to intercalate into DNA and inhibit cell proliferation upon activation by UVA radiation. PUVA therapy is generally administered twice weekly. Unfortunately, PUVA commonly causes short-term risks such as nausea, erythema, headache and skin pain as well as long-term risks of actinic keratoses, premature ageing of the skin, irregular pigmentation and squamous cell carcinoma which is reported in a quarter of patients (Stern, R. S., 1994, Cancer 73:2759-2764).

Systemic agents currently used to treat psoriasis include methotrexate (MTX), cyclosporin, acitretin and hydroxyurea. There are adverse side effects associated with each of these agents, however, and most are unavailable to pregnant patients. In particular, methotrexate, which is considered to be the 'gold standard' for treatment of severe psoriasis, carries a risk of hepatotoxicity with long-term use. In addition, it is recommended that patients have a liner biopsy performed at or near the start of each treatment and after each cumulative dose of 1.0-1.5 mg MTX (Roenigk, H. H. et al., 1988, J. of the Am. Acad. of Dermatology).

When patients are provided with information regarding the possible adverse effects of the currently available therapies for psoriasis, many often choose to live with the condition rather than undergo treatment (Greaves M. W., 1995, New England J. of Medicine 332:581-588). Other alternative treatments known in the art for dermatitis are based on hydrogenated vegetable oils, hydrophilic petrolatum, or medicated shampoos (based on zinc-pyrithione, selenium sulfide, sulfur and the like) in the case of seborrheic dermatitis, and are often unsuccessful.

There remains a great need for therapies with improved activity than currently available drugs and treatment regimens for the prevention, treatment or amelioration of dermatological diseases and disorders such as dermatitis and psoriasis.

SUMMARY OF THE INVENTION

The present invention is directed to a composition suitable for topical administration, which composition comprises Telmesteine, or a pharmaceutically acceptable salt thereof, as the active ingredient, and a pharmaceutically acceptable carrier or excipient. The present invention is also directed to a composition suitable for topical administration, which composition consists essentially of Telmesteine, or a pharmaceutically acceptable salt thereof, as the active ingredient, and a pharmaceutically acceptable carrier or excipient. In certain embodiments, the composition is suitable for topical administration and is in the form of a cream, gel, lotion, suspension, spray or ointment.

The present invention is directed to a method of treating or preventing a dermatological disease or disorder comprising topically administering to the site of the dermatological disease or disorder a composition comprising Telmesteine, or a pharmaceutically acceptable salt thereof, as the active ingredient, and a pharmaceutically acceptable carrier or excipient in an amount effective to treat or prevent such disease or disorder. In another embodiment, the present invention is directed to a method of treating or preventing a dermatological disease or disorder comprising topically administering to the site of the dermatological disease or disorder a composition consisting essentially of Telmesteine, or a pharmaceutically acceptable salt thereof, as the active ingredient, and a pharmaceutically acceptable carrier or excipient in an amount effective to treat or prevent such disease or disorder.

The present invention is directed to a method of ameliorating at least one symptom of a dermatological disease or disorder comprising topically administering to the site of the dermatological disease or disorder a composition comprising Telmesteine, or a pharmaceutically acceptable salt thereof, as the active ingredient, and a pharmaceutically acceptable carrier or excipient in an amount effective to ameliorate at least one symptom associated with such disease or disorder. In another embodiment, the present invention is directed to a method of ameliorating at least one symptom of a dermatological disease or disorder comprising topically administering to the site of the dermatological disease or disorder a composition consisting essentially of Telmesteine, or a pharmaceutically acceptable salt thereof, as the active ingredient, and a pharmaceutically acceptable carrier or excipient in an amount effective to ameliorate at least one symptom of such disease or disorder.

More particularly, the compositions of the present invention are also useful as moisturizers and lenitives for sensitive, delicate skins or to treat or ameliorate allergic irritations caused by medicaments, detergents, solvents; treat, prevent or ameliorate erythema subsequent to excessive exposure to sun radiation. In other embodiments of the present invention are useful in treating or ameliorating effects caused by insect bites, redness of various origin, post-shaving irritations, slight burns, cutaneous hyper-reactivity, as well as a normalizer after treatments of aesthetic medicine, such as skin peeling with glycolic acid or laser therapy. Additional exemplary dermatological diseases and disorders that can be treated or prevented in accordance with the present invention are listed infra.

In alternative embodiment, the present invention is directed to the use of Telmesteine for the preparation of a topical medicament for the treatment or prevention of a dermatological disease or disorder. In yet another embodiment, the present invention is directed to the use of Telmesteine for the preparation of a topical medicament for the amelioration of at least one symptom of a dermatological disease or disorder. In specific aspects of this embodiment, the disease or disorder is selected from the group consisting of atopic dermatitis (eczema), allergic contact dermatitis, seborrheic dermatitis, radiation dermatitis, psoriasis, xerosis and atopy.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a non-primate (e.g., a monkey such as a cynomolgous monkey and a human), and more preferably a human.

As used herein, the terms "prevent", "preventing" and prevention refer to the prevention of the recurrence or onset of one or more symptoms of a dermatological disease or disorder in a subject resulting from the administration of a prophylactic or therapeutic agent, i.e., Telmesteine. As used herein, the term "prophylactically effective amount" refers to that amount of the prophylactic agent sufficient to result in the prevention of the recurrence or onset of one or more symptoms of a disorder.

As used herein, the terms "treat", "treatment" and "treating" refer to the amelioration of one or more symptoms associated with a dermatological disease or disorder that results from the administration of a composition of the present invention. In certain embodiments, such amelioration includes, e.g., a reduction in the erythema, edema, oozing, scaling or crusting lesions and/or intense itching of the skin. In other embodiments, amelioration also includes the elimination of, or a reduction in the amount of, one or more traditional medications used in treating the disease or disorder, such as corticosteroids. Thus, in certain embodiments where a composition of the invention is topically administered separately with one or more traditional medications, the amount of the traditional medication necessary is reduced due to co-administration with a composition of the invention comprising Telmesteine.

The present invention can be more fully explained by reference to the following detailed description and illustrative examples.

DETAILED DESCRIPTION OF THE INVENTION

Surprisingly, the topical administration of a composition comprising or consisting essentially of an effective amount of Telmesteine, or a pharmaceutically acceptable salt thereof, as the active ingredient, provides an effective therapeutical or preventive treatment for a variety of dermatological diseases and disorders.

Accordingly, the present invention is directed to a composition suitable for topical administration, which composition comprises Telmesteine, or a pharmaceutically acceptable salt thereof, as the active ingredient, and a pharmaceutically acceptable carrier or excipient. The present invention is also directed to a composition suitable for topical administration, which composition consists essentially of Telmesteine, or a pharmaceutically acceptable salt thereof, as the active ingredient, and a pharmaceutically acceptable carrier or excipient. In certain embodiments, the composition is in the form of a cream, gel, lotion, suspension, spray or ointment.

The compositions of the invention can be used by themselves or in admixture with one or more medicaments, excipients and/or adjuvants, preferably forming a viscous and lubricating substance that remains adherent to the surface epithelium. These compositions are suitable for topical administration to epithelial surfaces such as the skin.

Optionally, the compositions of the present invention may further contain one or more other ingredients, such as an antibacterial, disinfectant, antifungal, analgesic, emollients, local anaesthetics and the like. Suitable antimicrobials include, but are not limited to, quaternary ammonium salts such as benzalkonium chloride. In particular embodiments, the compositions of the invention do not contain a proanthrocyanidin compound and/or glycyrrhetinic acid.

Various topical delivery systems are known and can be used to administer a composition of the present invention, e.g., encapsulation in liposomes, microparticles, microcapsules, etc. In preferred embodiments, it is desirable to administer the pharmaceutical compositions of the invention locally to the area in need of treatment; this may be achieved by, for example, and not by way of limitation, topical application, e.g., in conjunction with a wound dressing after surgery, by means of a suppository, or by means of an implant, said implant being of a porous, non-porous, or gelatinous material, including membranes, such as sialastic membranes, or fibers.

For topical administration, the compositions can be formulated in the form of, e.g., an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well-known in the art.

In another embodiment, the composition of the invention can be delivered in a vesicle, in particular a liposome (see Langer, Science 249:1527 1533 (1990); Treat et al., in Liposomes in the Therapy of Infectious Disease and Cancer, Lopez-Berestein and Fidler (eds.), Liss, New York, pp. 353 365 (1989); Lopez Berestein, ibid., pp. 317 327; see generally ibid.). In preferred embodiments, the compositions of the present invention do not contain allergenic substances, derivatives from animal sources (such as lanolin, beeswax, animal fat), and certain preservatives (such as parabens, isothiazolones, phenol derivatives, and the like) which are often responsible for allergic contact dermatitis.

Examples of pharmaceutically acceptable salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound having an acidic functional group, such as a carboxylic acid or sulfonic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis- or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

The present invention is also directed to a method of treating or preventing a dermatological disease or disorder comprising topically administering to the site of the dermatological disease or disorder a composition comprising Telmesteine, or a pharmaceutically acceptable salt thereof, as the active ingredient, and a pharmaceutically acceptable carrier or excipient in an amount effective to treat or prevent such disease or disorder. In another embodiment, the present invention is directed to a method of treating or preventing a dermatological disease or disorder comprising topically administering to the site of the dermatological disease or disorder a composition consisting essentially of Telmesteine, or a pharmaceutically acceptable salt thereof, as the active ingredient, and a pharmaceutically acceptable carrier or excipient in an amount effective to treat or prevent such disease or disorder.

The present invention is directed to a method of ameliorating at least one symptom of a dermatological disease or disorder comprising topically administering to the site of the dermatological disease or disorder a composition comprising Telmesteine, or a pharmaceutically acceptable salt thereof, as the active ingredient, and a pharmaceutically acceptable carrier or excipient in an amount effective to ameliorate at least one symptom associated with such disease or disorder. In another embodiment, the present invention is directed to a method of ameliorating at least one symptom of a dermatological disease or disorder comprising topically administering to the site of the dermatological disease or disorder a composition consisting essentially of Telmesteine, or a pharmaceutically acceptable salt thereof, as the active ingredient, and a pharmaceutically acceptable carrier or excipient in an amount effective to ameliorate at least one symptom of such disease or disorder.

More particularly, the compositions of the present invention are useful for the treatment or prevention of pathologies such as irritative and eczematous dermatitis, as moisturizers and lenitive for sensitive, delicate skins; in allergic irritations caused by medicaments, detergents, solvents; in erythema subsequent to excessive exposure to sun radiations; in case of insect bites, redness of various origin, post-shaving irritations, slight burns, cutaneous hyper-reactivity; as normalizers after treatments of aesthetic medicine, such as peeling with glycolic acid or laser therapy. Exemplary, non-limiting dermatological diseases and disorders include, but are not limited to, dermatitis conditions and skin impairments such as atopic dermatitis, contact dermatitis, allergic contact dermatitis, allergic dermatitis, seborrheic dermatitis, nummular dermatitis, chronic dermatitis of hands or feet, generalized exfoliative dermatitis, stasis dermatitis, neonatal dermatitis, pediatric dermatitis, localized scratch dermatitis, toxic/irritating contact eczema, allergic contact eczema, type I or type IV photoallergic contact eczema, contact urticaria, dyshidrosiform eczema, age-caused wrinkles, sun damage and itching.

Other dermatological disorders which may be treated by a composition of the present invention, include:
  Psoriasis: psoriasis vulgaris, flaking eczema, psoriasis pustulosa, psoriasis arthropatica, psoriatic erythroderma;
  Rosacea;
  Photodermatosis: radiodermatitis acuta and chronica (UV and ionizing radiation therapy), chronic actinic dermatitis, photouticaria (uticaria solaris), polymorphic photodermatosis;
  Prurigo: p. simplex acuta (strophulus, uticaria papulosa), subacuta, chronic;
  Acne: acne vulgaris, juvenile and adult (acne with comedones, papulous, pustulous, nodose, i.e., nodular, nodulocystic acne), acne conglobata (special form: hidradenitis suppurativa), acne fulminans, acne tetrad, acne neonatorum, senile acne, mechanical acne forms (excoriated acne), acne cosmetica, folliculitis with superinfected acne (*Staphylococci*), occupation-related acne forms (for example chlorine acne);
  Decubitis and Ulcus cruris;
  Deficient ipoactive skin: localized scratch dermatitis rinophyma, ichthyosis, xerosis;
  Perioral dermatitis.

The precise dose to be employed in the composition will depend on the seriousness of the disease or disorder, and should be decided according to the judgment of the practitioner and each patient's circumstances. In principle, however, a cream, lotion or ointment containing about 0.001% to about 50% Telmesteine, or a pharmaceutically acceptable salt thereof, in an oil base or an emulsion base, including oil-in-water type and water-in-oil type emulsions, applied two to three times or more daily, will be sufficient to provide an optimal therapeutic or preventive response. The treatment can be protracted until remission of symptoms, usually for at least 2 days, but preferably 5-10 days. More prolonged treatments are not contraindicated, considering the low, if any, toxicity of the components of the compositions of the invention. In preferred embodiments, the composition of the invention contains about 0.01% to about 25% Telmesteine, about 0.1% to about 10% Telmesteine, about 0.1% to about 5% Telmesteine, about 0.1% to about 2% Telmesteine, about 0.1% to about 1% Telmesteine, or about 0.5% to about 1% Telmesteine or a pharmaceutically acceptable salt thereof. In other preferred embodiments, the composition of the invention contains about 0.01%, 0.1%, 0.5%, 1%, 2%, 5%, 10%, 20%, 25% Telmesteine or a pharmaceutically acceptable salt thereof.

In alternative embodiments, other active ingredients can be co-administered to treat or prevent a dermatological disease or disorder in the same composition with Telmesteine or in a separate composition. Preferably, the additional active ingredients are co-administered in a separate pharmaceutical composition. In other embodiments, the additional active ingredients are co-administered in a separate composition at the same time or a later time as administration of a composition of the present invention containing Telmesteine or a pharmaceutically acceptable salt thereof. Examples of other topical agents include, but are not limited to emolliments, salicyclic acid, coal tar, anthralins, topical steroids, topical corticosteroids (e.g., difloroasone diacetate, clobetasol propionate, halobetasol propionate, betamethasone dipropionate, fluocinonide, halcinonide desoximetasone, triamcinolone, fluticasone propionate, fluocinolone acetonide, flurandrenolide, mometasone furoate, betamethosone, fluticasone propionate, fluocinolone acetonide, aclometasome dipropionate, desonide and hydrocortisone), topical vitamin D3 analogs (e.g., calcipotriene), topical retinoids (e.g., tazarotene). In certain embodiments, another agent is a systemically administered agent. Examples of agents administered systemically include, but are not limited to, systemic corticosteroids (e.g., triamcinalone), folic acid antagonists (e.g., methotrexate), retinoids (e.g., acetretin) and cyclosporine.

The present invention also provides a pharmaceutical pack or kit comprising one or more containers, e.g., a tube, vial, ampoule, bottle and the like, filled with one or more of the ingredients of the compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a preferred embodiment, the compositions of the present invention can be presented as single- or multi-dose forms in a flexible packet. Preferably, the compositions of the present invention are packaged as a cream suitable for topical administration for use by the patient.

The following examples illustrate the invention in more detail.

EXAMPLE 1

Telmesteine Cream (0.01% by Weight)

| | |
|---|---|
| Telmesteine | 0.01% |
| Sodium hyaluronate | 0.1% |
| Ethylhexyl palmitate | 10.1% |
| Pentylene glycol | 6.0% |
| Arachidyl alcohol, behenyl alcohol, arachidyl glycoside | 4.5% |
| Glyceryl stearate, PEG-100 stearate | 4.5% |
| Butylene glycol | 4.5% |
| Capriloyl glycine | 2.5% |
| Tocopheryl acetate | 1.2% |
| Carbomer | 1.7% |
| Ethylhexyl glycerin | 1.6% |
| Piroctone olamine | 0.5% |
| Sodium hydroxide | 0.387% |
| Allantoin | 0.85% |
| DMDM hydantoin | 0.3% |
| EDTA disodium salt | 0.08% |
| Tetrahexyldecyl ascorbate | 0.05% |

| -continued | |
|---|---|
| Propyl gallate | 0.02% |
| Water | 61.103% |
| Total | 100.0% |

EXAMPLE 2

Telmesteine Cream (0.01% by Weight)

| | |
|---|---|
| Telmesteine | 0.01% |
| Ethylhexyl palmitate | 11.0% |
| Pentylene glycol | 7.0% |
| Arachidyl alcohol, behenyl alcohol, arachidyl glycoside | 4.0% |
| Glyceryl stearate, PEG-100 stearate | 4.0% |
| Butylene glycol | 4.0% |
| Capriloyl glycine | 2.5% |
| Tocopheryl acetate | 2.0% |
| Salicylic acid | 1.0% |
| Sodium hydroxide | 0.785% |
| Carbomer | 1.8% |
| Ethylhexyl glycerin | 0.6% |
| Allantoin | 0.35% |
| DMDM hydantoin | 0.3% |
| EDTA disodium salt | 0.08% |
| Tetrahexyldecyl ascorbate | 0.05% |
| Propyl gallate | 0.02% |
| Water | 59.805% |
| Total | 100.0% |

EXAMPLE 3

Telmesteine Cream (2% by Weight)

| | |
|---|---|
| Telmesteine | 2.0% |
| Ethylhexyl palmitate | 10.0% |
| Pentylene glycol | 6.1% |
| Arachidyl alcohol, behenyl alcohol, arachidyl glycoside | 5.0% |
| Glyceryl stearate, PEG-100 stearate | 4.0% |
| Butylene glycol | 4.0% |
| Capriloyl glycine | 2.5% |
| Tocopheryl acetate | 1.0% |
| Sodium hydroxide | 0.762% |
| Carbomer | 0.7% |
| Ethylhexyl glycerin | 0.6% |
| Piroctone olamine | 0.5% |
| Allantoin | 0.35% |
| DMDM hydantoin | 0.3% |
| Sodium hyaluronate | 0.1% |
| EDTA disodium salt | 0.08% |
| Tetrahexyldecyl ascorbate | 0.05% |
| Propyl gallate | 0.02% |
| Water | 61.938% |
| Total | 100.0% |

EXAMPLE 4

Thirty patients are evaluated. All patients in the study are affected with dermatitis of various causes.

Patients are treated with the composition described in Example 1. The composition is topically applied to the site of dermatitis for one to four times a day.

At the end of the treatment, the extent of the dermatitis is evaluated. The use of the composition will show a reduction in the severity of the dermatitis as evaluated by any of the following factors: redness, inflammation, dryness, itchiness, scaling, etc., of the skin.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled. Such modifications are intended to fall within the scope of the appended claims.

All references, patent and non-patent, cited herein are incorporated herein by reference in their entireties and for all purposes to the same extent as if each individual publication or patent or patent application was specifically and individually indicated to be incorporated by reference in its entirety for all purposes.

The invention claimed is:

1. A pharmaceutical composition consisting essentially of 0.01% Telmesteine, 0.1% sodium hyaluronate, 10.1% ethylhexyl palmitate, 6.0% pentylene glycol, 4.5% arachidyl alcohol, behenyl alcohol, arachidyl glycoside, 4.5% glyceryl stearate PEG-100 stearate, 4.5% butylene glycol, 2.5% capriloyl glycine, 1.2% tocopheryl acetate, 1.7% carbomer, 1.6% ethylhexyl glycerin, 0.5% piroctone olamine, 0.387% sodium hydroxide, 0.85% allantoin, 0.3% DMDM hydantoin, 0.08% EDTA disodium salt, 0.05% tetrahexyldecyl ascorbate, 0.02% propyl gallate, and 61.103% water.

2. A pharmaceutical composition consisting essentially of 0.01% Telmesteine, 11.0% ethylhexyl palmitate, 7.0% pentylene glycol, 4.0% arachidyl alcohol, behenyl alcohol, arachidyl glycoside, 4.0% glyceryl stearate, PEG-100 stearate, 4.0% butylene glycol, 2.5% capriloyl glycine, 2.0% tocopheryl acetate, 1.0% salicylic acid, 0.785% sodium hydroxide, 1.8% carbomer, 0.6% ethylhexyl glycerin, 0.35% allantoin, 0.3% DMDM hydantoin, 0.08% EDTA disodium salt, 0.05% tetrahexyldecyl ascorbate, 0.02% propyl gallate, and 59.805% water.

3. A pharmaceutical composition consisting essentially of 2.0% Telmesteine, 10.0% ethylhexyl palmitate, 6.1% pentylene glycol, 5.0% arachidyl alcohol, behenyl alcohol, arachidyl glycoside, 4.0% glyceryl stearate, PEG-100 stearate, 4.0% butylene glycol, 2.5% capriloyl glycine, 1.0% tocopheryl acetate, 0.762% sodium hydroxide, 0.7% carbomer, 0.6% ethylhexyl glycerin, 0.5% piroctone olamine, 0.35% allantoin, 0.3% DMDM hydantoin, 0.1% sodium hyaluronate, 0.08% EDTA disodium salt, 0.05% tetrahexyldecyl ascorbate, 0.02% propyl gallate, and 61.938% water.

4. A method treating a dermatological disease or disorder selected from age-caused wrinkles, rosacea and acne comprising topically administering to the site of the dermatological disease or disorder a composition comprising Telmesteine in an amount effective to treat or prevent such disease or disorder.

5. The method of claim 4, wherein the composition consists essentially of Telmesteine and a pharmaceutically acceptable carrier.

6. The method of claim 4, wherein the composition further comprises a surfactant, stabilizing agent/preservative, fragrance, or a co-solubilizer.

7. The method of claim 4, further comprising topically administering a second composition comprising an additional active agent effective to treat or prevent a dermatological disease or disorder.

8. The method of claim 4, wherein the composition does not comprise proanthrocyanadin or glycyrrhetinic acid.

9. The method of claim 4, wherein the composition is in the form of a cream, gel, lotion, suspension, spray or ointment.

10. The method of claim 4, further comprising an antibacterial agent, disinfectant agent, antifungal agent, analgesic, emollient, or a local anesthetic.

* * * * *